(12) United States Patent
Saeki et al.

(10) Patent No.: US 11,077,400 B2
(45) Date of Patent: Aug. 3, 2021

(54) DEHUMIDIFIER

(71) Applicant: NIHON KOHDEN CORPORATION, Tokyo (JP)

(72) Inventors: Kota Saeki, Tokorozawa (JP); Muneshige Kurahashi, Nishitokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 238 days.

(21) Appl. No.: 16/375,978

(22) Filed: Apr. 5, 2019

(65) Prior Publication Data

US 2019/0344215 A1 Nov. 14, 2019

(30) Foreign Application Priority Data

May 8, 2018 (JP) .............................. JP2018-089955

(51) Int. Cl.
*B01D 53/26* (2006.01)
*B01D 53/22* (2006.01)
*A61B 5/097* (2006.01)
*B01D 63/02* (2006.01)

(52) U.S. Cl.
CPC ............ *B01D 53/268* (2013.01); *A61B 5/097* (2013.01); *B01D 53/22* (2013.01); *B01D 63/02* (2013.01); *B01D 2053/224* (2013.01)

(58) Field of Classification Search
None
See application file for complete search history.

(56) References Cited

U.S. PATENT DOCUMENTS

| 6,156,096 A * | 12/2000 | Sirkar | B01D 53/22 |
| | | | 95/44 |
| 6,346,142 B1 * | 2/2002 | Jetter | B01D 53/268 |
| | | | 96/10 |
| 2012/0186328 A1 | 7/2012 | Makino et al. | |
| 2014/0220462 A1 * | 8/2014 | Takeda | B01D 53/268 |
| | | | 429/410 |

FOREIGN PATENT DOCUMENTS

JP 2012-163544 A 8/2012

* cited by examiner

*Primary Examiner* — Jason M Greene
(74) *Attorney, Agent, or Firm* — Pearne & Gordon, LLP

(57) ABSTRACT

A dehumidifier is connected to a respiratory gas measuring apparatus. A membrane dryer has a first flow path through which a respiratory gas of a subject passes, and a second flow path through which a purge gas passes. A first normally-closed electromagnetic valve is disposed in a first upstream flow path that communicates with the first flow path. A second normally-closed electromagnetic valve is disposed in a first downstream flow path that communicates with the first flow path. A third normally-closed electromagnetic valve is disposed in a second upstream flow path that communicates with the second flow path. A fourth normally-closed electromagnetic valve is disposed in a second downstream flow path that communicates with the second flow path.

6 Claims, 3 Drawing Sheets

DEHUMIDIFIER

CROSS-REFERENCE TO RELATED APPLICATIONS

This application is based on and claims priority under 35 USC 119 from Japanese Patent Application No. 2018-089955 filed on May 8, 2018, the contents of which are incorporated herein by reference.

TECHNICAL FIELD

The presently disclosed subject matter relates to a dehumidifier which is to be connected to a respiratory gas measuring apparatus for measuring a respiratory gas of a subject.

BACKGROUND ART

Patent Literature 1 discloses an example of a respiratory gas measuring apparatus. In a measurement of a respiratory gas, the humidity difference between the expiration and inspiration of a subject may cause a measurement error. Therefore, it is proposed that the respiratory gas is dehumidified by passing the gas through a membrane dryer having a hollow fiber membrane, thereby reducing the humidity difference between the expiration and the inspiration.

CITATION LIST

Patent Literature

Patent Literature 1: JP-A-2012-163544

SUMMARY OF INVENTION

In order to perform dehumidification such as described above, the hollow fiber membrane must be first set to a dry state. However, such a hollow fiber membrane has a large water content capacity, and therefore a long period of time is required to obtain a dry state. Namely, a long period of time elapses from activation of the dehumidifier to a timing when a correct measurement is enabled.

It is an object of the presently disclosed subject matter to shorten a period of time which elapses until a timing when a correct measurement of a respiratory gas is enabled.

A mode which can attain the object is a dehumidifier which is to be connected to a respiratory gas measuring apparatus, the dehumidifier includes:

a membrane dryer having a first flow path through which a respiratory gas of a subject passes, and a second flow path through which a gas that is smaller in water content than the respiratory gas passes;

a first normally-closed electromagnetic valve which is disposed in a first upstream flow path that communicates with the first flow path;

a second normally-closed electromagnetic valve which is disposed in a first downstream flow path that communicates with the first flow path;

a third normally-closed electromagnetic valve which is disposed in a second upstream flow path that communicates with the second flow path; and a fourth normally-closed electromagnetic valve which is disposed in a second downstream flow path that communicates with the second flow path.

When a power supply to the dehumidifier is cut off after a measurement of a respiratory gas is ended, all of the first normally-closed electromagnetic valve, the second normally-closed electromagnetic valve, the third normally-closed electromagnetic valve, and the fourth normally-closed electromagnetic valve are set to a closed state. Namely, each of the first upstream flow path, the first downstream flow path, the second upstream flow path, and the second downstream flow path is closed. This causes the communications between the first flow path and the second flow path, and the ambient air to be interrupted.

According to the configuration, when the dehumidifier is not activated, the membrane of the membrane dryer can be prevented from absorbing the humidity of the ambient air. In other words, the water content of the membrane can be suppressed from increasing during a period when a measurement of the respiratory gas is not performed. Therefore, it is possible to, at reactivation of the dehumidifier, shorten a period of time which elapses before a correct measurement of a respiratory gas is enabled.

DESCRIPTION OF EMBODIMENTS

Figure 1:
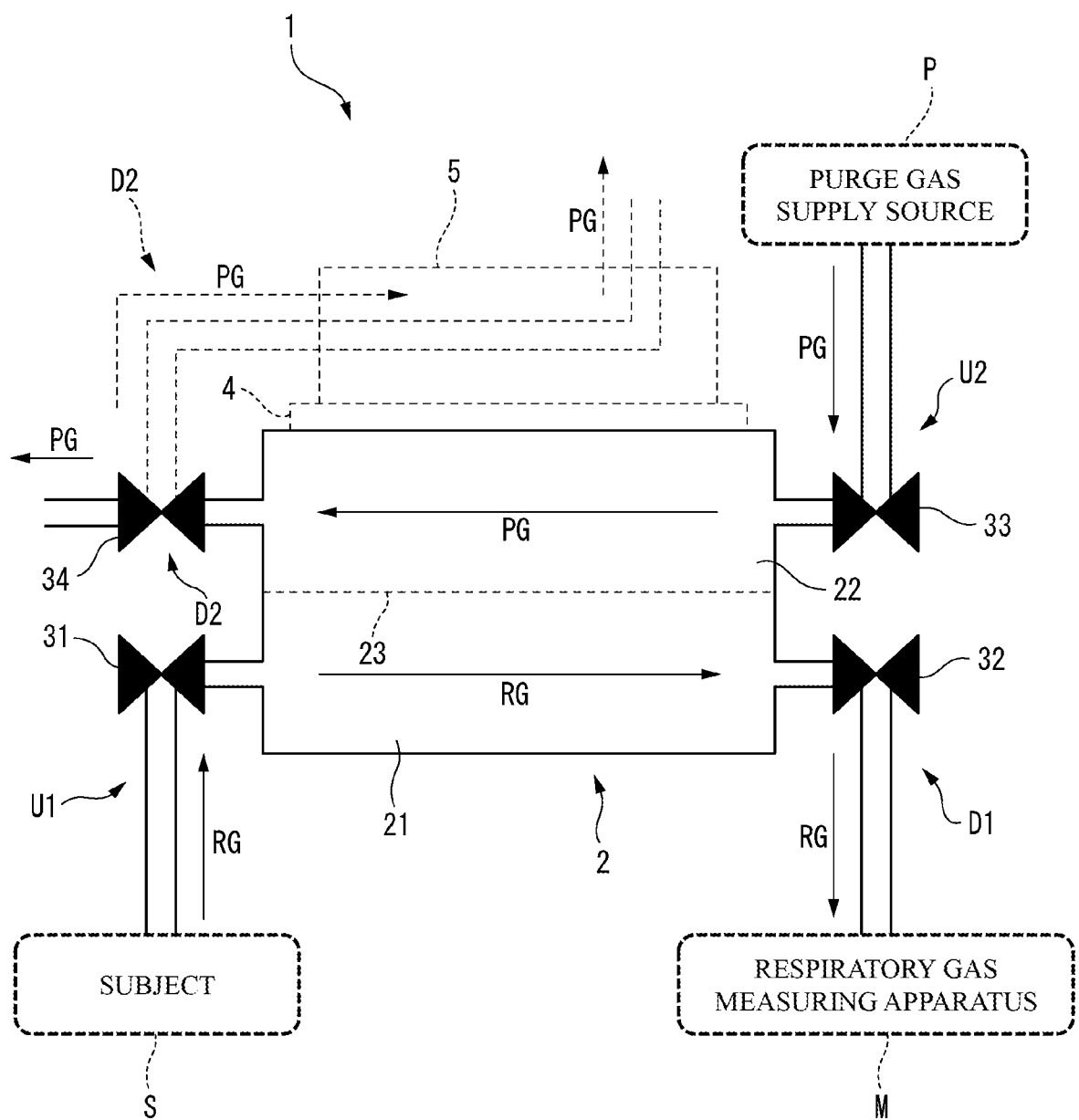
FIG. 1 diagrammatically illustrates the configuration of a dehumidifier of an embodiment.

An embodiment will be described in detail with reference to the accompanying drawings. In the drawings, in order to make the components to be described, to have a recognizable size, their scales are appropriately changed.

FIG. 1 diagrammatically illustrates the configuration of a dehumidifier 1 of the embodiment. The dehumidifier 1 is connected to a respiratory gas measuring apparatus M which measures the respiratory gas of a subject S.

The dehumidifier 1 may include a membrane dryer 2. The membrane dryer 2 may include a first flow path 21, a second flow path 22, and a membrane 23. The membrane 23 is formed by a hollow fiber membrane which is made of, for example, a fluorine resin. The membrane 23 separates the first flow path 21 and the second flow path 22 from each other.

The first flow path 21 is a flow path through which the respiratory gas RG of the subject S is allowed to pass. The respiratory gas RG is a gas which is to be measured by the respiratory gas measuring apparatus M.

The second flow path 22 is a flow path through which a purge gas PG is allowed to pass. The dehumidifier 1 is connected also to a purge gas supply source P. The purge gas PG is supplied from the purge gas supply source P. The purge gas supply source P may be the atmospheric air. The purge gas PG is an example of the gas that is smaller in water content than the respiratory gas RG.

The membrane 23 has an affinity for water molecules. The respiratory gas RG which enters the first flow path 21 is larger in water content than the purge gas PG that enters the second flow path 22. Therefore, there is a water vapor partial pressure difference between the respiratory gas RG and purge gas PG which flow across the membrane 23. As a result, a force for equalizing the water vapor partial pressures is generated in the membrane 23. This force causes the water in the respiratory gas RG to pass through the membrane 23 to transfer into the second flow path 22, thereby dehumidifying the gas.

The dehumidifier 1 may further include a first normally-closed electromagnetic valve 31. The first normally-closed electromagnetic valve 31 is disposed in an arbitrary place in a first upstream flow path U1. The first upstream flow path U1 is a flow path which causes the subject S and the first flow path 21 to communicate with each other, and which supplies the respiratory gas RG to the membrane dryer 2. The first normally-closed electromagnetic valve 31 is connected to a power supply which is not shown. The first normally-closed electromagnetic valve 31 is an electromagnetic valve which, when the valve is not energized, is set to a closed state.

The dehumidifier 1 may further include a second normally-closed electromagnetic valve 32. The second normally-closed electromagnetic valve 32 is disposed in an arbitrary place in a first downstream flow path D1. The first downstream flow path D1 is a flow path which causes the first flow path 21 and the respiratory gas measuring apparatus M to communicate with each other, and which supplies the respiratory gas RG that has passed through the membrane dryer 2, to the respiratory gas measuring apparatus M. The second normally-closed electromagnetic valve 32 is connected to the power supply which is not shown. The second normally-closed electromagnetic valve 32 is an electromagnetic valve which, when the valve is not energized, is set to a closed state.

The dehumidifier 1 may further include a third normally-closed electromagnetic valve 33. The third normally-closed electromagnetic valve 33 is disposed in an arbitrary place in a second upstream flow path U2. The second upstream flow path U2 is a flow path which causes the purge gas supply source P and the second flow path 22 to communicate with each other, and which supplies the purge gas PG to the membrane dryer 2. The third normally-closed electromagnetic valve 33 is connected to the power supply which is not shown. The third normally-closed electromagnetic valve 33 is an electromagnetic valve which, when the valve is not energized, is set to a closed state.

The dehumidifier 1 may further include a fourth normally-closed electromagnetic valve 34. The fourth normally-closed electromagnetic valve 34 is disposed in an arbitrary place in a second downstream flow path D2. The second downstream flow path D2 is a flow path for discharging the purge gas PG that has passed through the membrane dryer 2. The fourth normally-closed electromagnetic valve 34 is connected to the power supply which is not shown. The fourth normally-closed electromagnetic valve 34 is an electromagnetic valve which, when the valve is not energized, is set to a closed state.

When the thus configured dehumidifier 1 is activated, an electric power is supplied to the first normally-closed electromagnetic valve 31, the second normally-closed electromagnetic valve 32, the third normally-closed electromagnetic valve 33, and the fourth normally-closed electromagnetic valve 34, and the valves are set to the opened state.

Therefore, the respiratory gas RG of the subject S is supplied to the first flow path 21 of the membrane dryer 2 through the first upstream flow path U1. On the other hand, the purge gas PG is supplied to the second flow path 22 of the membrane dryer 2 through the second upstream flow path U2.

As described above, the water contained in the respiratory gas RG which enters into the first flow path passes through the membrane 23 to transfer into the second flow path 22. The dehumidified respiratory gas RG which has passed through the first flow path 21 is supplied to the respiratory gas measuring apparatus M through the first downstream flow path D1, and then subjected to a measurement. The humidity difference between the expiration and inspiration of the subject S is reduced by the membrane dryer 2, and therefore the measurement error can be suppressed from being generated in the respiratory gas measuring apparatus M.

On the other hand, the purge gas PG which has passed through the membrane dryer 2 is discharged through the second downstream flow path D2.

When the power supply to the dehumidifier 1 is cut off after the measurement of the respiratory gas is ended, all of the first normally-closed electromagnetic valve 31, the second normally-closed electromagnetic valve 32, the third normally-closed electromagnetic valve 33, and the fourth normally-closed electromagnetic valve 34 are set to the closed state. Namely, each of the first upstream flow path U1, the first downstream flow path D1, the second upstream flow path U2, and the second downstream flow path D2 is closed. This causes the communication between the first flow path 21 and second flow path 22 of the membrane dryer 2, and the ambient air to be interrupted.

According to the configuration, when the dehumidifier 1 is not activated, the membrane 23 of the membrane dryer 2 can be prevented from absorbing the water vapor of the ambient air. In other words, the water content of the membrane 23 can be suppressed from increasing during a period when the measurement of the respiratory gas is not performed. In the case where the dehumidifier 1 is reactivated, therefore, a period of time which elapses before a dry state of the membrane 23 is attained can be shortened. Namely, it is possible to shorten a period of time which elapses before a correct measurement of the respiratory gas is enabled.

Figure 2:
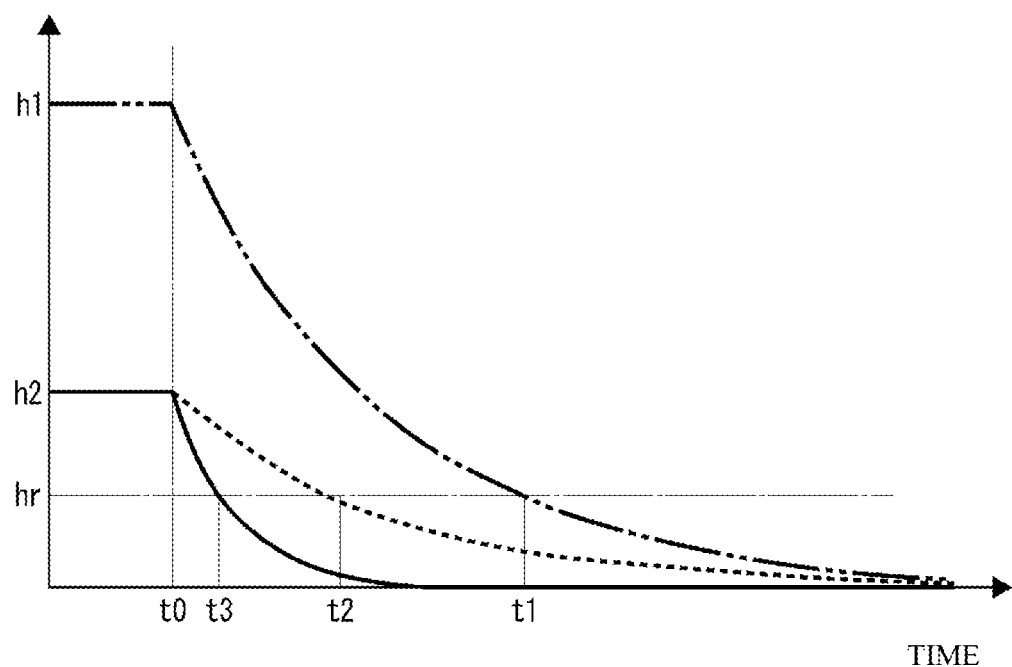
FIG. 2 illustrates an effect which is attained by the dehumidifier.

FIG. 2 illustrates the temporal change of the humidity which is measured in the first downstream flow path D1. The dash-dot-dash line indicates a change which is obtained in the case where only the membrane dryer 2 is used, as a comparative example. The broken line indicates a change in the embodiment in the case where the four normally-closed electromagnetic valves are combined with the membrane dryer 2.

When the dehumidifier 1 is activated as timing t0, the humidity h1 of the first downstream flow path D1 in the comparative example is equivalent to that of the ambient air. In the embodiment, the communication between the interior of the membrane dryer 2 and the ambient air is interrupted by the four normally-closed electromagnetic valves, and therefore the humidity h2 of the first downstream flow path D1 at timing t0 is lower than that of the comparative example.

The reference character hr indicates the humidity which is required for performing a correct measurement of the respiratory gas. The supply of the purge gas PG after the activation of the dehumidifier 1 causes the membrane 23 of the membrane dryer 2 to be dried, and the humidity of the first downstream flow path D1 is gradually lowered. In the comparative example, the humidity reaches the required value hr at timing t1. In the embodiment, the humidity reaches the required value hr at timing t2. It is seen that the initial value h2 of the humidity at the activation of the dehumidifier 1 is low, and therefore a period of time which elapses before the humidity reaches the required value hr can be shortened as compare with the comparative example.

As indicated by the broken lines in FIG. 1, the dehumidifier 1 may further include a cooling device 4. The cooling device 4 may be configured so as to cool the membrane dryer 2. The cooling device 4 may include, for example, a Peltier element.

When the transfers of water vapor both between the respiratory gas RG and the membrane 23, and between the membrane 23 and the purge gas PG achieve equilibrium, the dehumidification performed by the membrane 23 stops. At this time, a constant amount of water remains in the membrane 23. When the water vapor partial pressure of the respiratory gas RG is lowered to the residual water level in the membrane 23, therefore, the water vapor gradient between the respiratory gas RG and the membrane 23 is eliminated, and the dehumidification stops. Namely, the smaller the residual water amount of the membrane 23, the higher dehumidification power is obtained. The lower the temperature, the smaller residual water amount of the membrane 23. When the dehumidifier 2 is cooled as described above, therefore, the dehumidification power can be enhanced.

In the graph illustrated in FIG. 2, the solid line indicates the temporal change of the humidity in the first downstream flow path D1 in the case where, as in the embodiment, the dehumidifier 1 includes the cooling device 4. In the embodiment, the initial value h2 of the humidity is equal to that in the case of no cooling device, indicated by the broken line, but the humidity is lowered to the required value hr at timing t3 which is earlier than the corresponding timing in the case of no cooling device. It is seen that, when the state where the residual water amount of the membrane 23 is small is produced by the cooling device 4, the period of time which elapses before the humidity is lowered to the required value hr can be shortened. Namely, the period of time which elapses before a correct measurement of the respiratory gas is started can be further shortened.

As illustrated in FIG. 1, the dehumidifier 1 may further include a heat radiating member 5. The heat radiating member 5 may be configured so as to dissipate heat generated by the cooling device 4. In the case, the dehumidifier 1 is configured so that the purge gas PG which passes through the membrane dryer 2, and flows through the second downstream flow path D2 passes through the heat radiating member 5.

Figure 3:
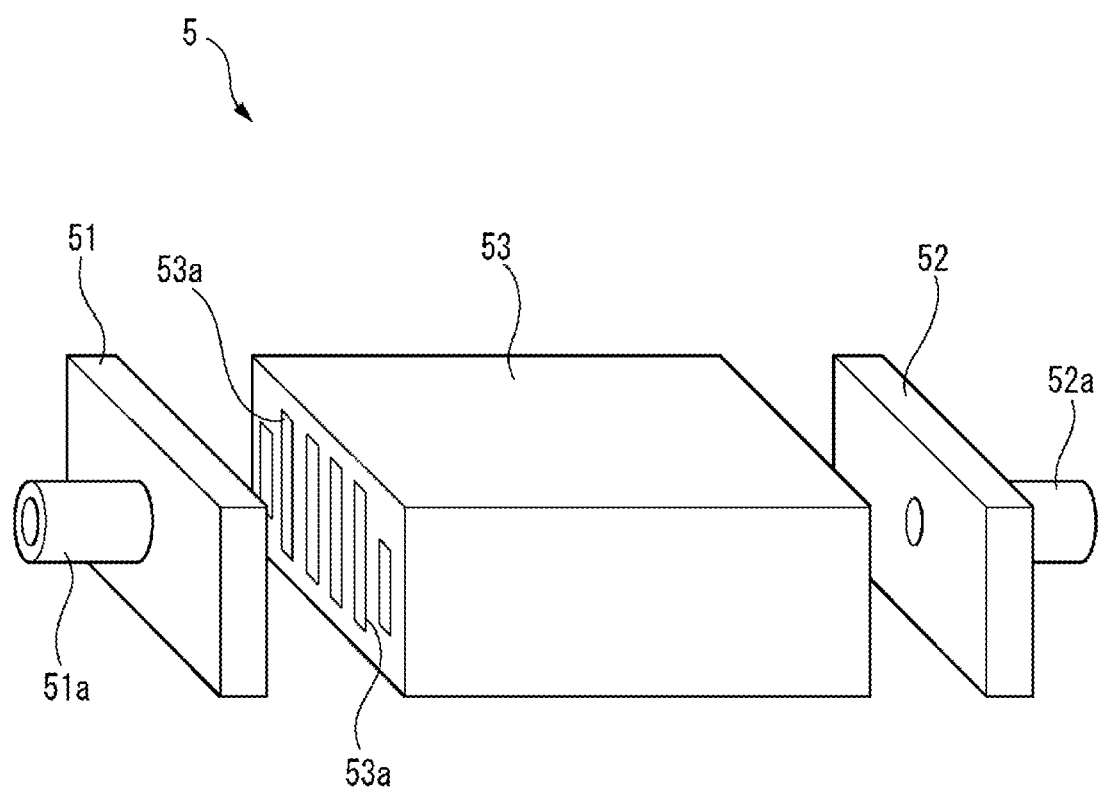
FIG. 3 illustrates an example of a heat radiating member disposed in the dehumidifier.

As illustrated in FIG. 3, the heat radiating member 5 may include a first connecting portion 51, a second connecting portion 52, and a heat sink 53. The heat sink 53 may be formed by an aluminum extruded member or the like so as to define a plurality of air passages 53a. The first connecting portion 51 and the second connecting portion 52 are coupled to the heat sink 53 by adequate means.

The first connecting portion 51 may have a pipe conduit 51a. The pipe conduit 51a is connected with the second downstream flow path D2. In a state where the first connecting portion 51 is coupled to the heat sink 53, the interior of the pipe conduit 51a communicates with the air passages 53a.

The second connecting portion 52 has a pipe conduit 52a. The pipe conduit 52a is connected with a discharge flow path. In a state where the second connecting portion 52 is coupled to the heat sink 53, the interior of the pipe conduit 52a communicates with the air passages 53a.

Preferably, the plurality of air passages 53a are formed so that, in the state where the first connecting portion 51 and the second connecting portion 52 are coupled to the heat sink 53, the purge gas PG flowing through the air passages is not in direct contact with the ambient air.

The purge gas PG enters from the pipe conduit 51a, flows through the air passages 53a, and flows out from the pipe conduit 52a. According to the configuration, the heat radiating member 5 can be cooled by using the flow of the purge gas PG. A cooling fan or the like for cooling the heat radiating member 5 is not necessary, and therefore the size and power consumption of the dehumidifier 1 can be suppressed from being increased.

Preferably, the purge gas PG which has passed through the heat radiating member 5 is discharged to the atmospheric air. After the purge gas PG passes through the membrane dryer 2, the gas contains the water which is removed from the respiratory gas RG. This purge gas PG is heated by passing through the heat radiating member 5, and therefore vapor condensation in the flow path can be prevented from occurring. Therefore, it is not necessary to dispose a device such as a water trap. Consequently, the size of the dehumidifier 1 can be suppressed from increasing, and moreover works such as replacement of the water trap and water disposal can be eliminated.

The above-described embodiment is a mere example for facilitating understanding of the disclosure. The configuration of the embodiment may be adequately changed or improved without departing from the spirit of the presently disclosed subject matter.

What is claimed is:

1. A dehumidifier which is to be connected to a respiratory gas measuring apparatus, the dehumidifier comprising:
   a membrane dryer having a first flow path through which a respiratory gas of a subject passes, a second flow path through which a gas that is smaller in water content than the respiratory gas passes, and a membrane that separates the first flow path and the second flow path from each other;
   a first normally-closed electromagnetic valve which is disposed in a first upstream flow path that communicates with the first flow path;
   a second normally-closed electromagnetic valve which is disposed in a first downstream flow path that communicates with the first flow path;
   a third normally-closed electromagnetic valve which is disposed in a second upstream flow path that communicates with the second flow path;
   a fourth normally-closed electromagnetic valve which is disposed in a second downstream flow path that communicates with the second flow path;
   a cooling device which cools the membrane dryer; and
   a heat radiating member which dissipates heat generated by the cooling device,
   wherein a gas which flows through the second downstream flow path passes through the heat radiating member.

2. The dehumidifier according to claim 1,
   wherein the gas which flows through the second downstream flow path is discharged after the gas passes through the heat radiating member.

3. The dehumidifier according to claim 1,
   wherein the membrane is configured by a hollow fiber membrane.

4. The dehumidifier according to claim 1,
   wherein the first, the second, the third, and the fourth normally-closed electromagnetic valves are respectively set to closed states when the first, the second, the third, and the fourth normally-closed electromagnetic valves are not energized.

5. The dehumidifier according to claim 1,
wherein the heat radiating member includes a plurality of air passages which are formed so that a purge gas is not in direct contact with an ambient air.

6. A system comprising:
the dehumidifier according to claim 1, and
the respiratory gas measuring apparatus,
wherein the respiratory gas measuring apparatus is connected to the dehumidifier.

* * * * *